US008802851B2

(12) United States Patent
Ferrari et al.

(10) Patent No.: US 8,802,851 B2
(45) Date of Patent: Aug. 12, 2014

(54) PROCESS FOR PREPARING VILAZODONE HYDROCHLORIDE

(71) Applicant: Erregierre S.p.A., San Paolo d'Argon (IT)

(72) Inventors: Massimo Ferrari, Cenate Sotto (IT); Daniele De Zani, Roncello (IT); Matteo Bonaldi, Schilpario (IT)

(73) Assignee: Erregierre S.p.A., San Paolo d'Argon (IT)

( * ) Notice: Subject to any disclaimer, the term of this patent is extended or adjusted under 35 U.S.C. 154(b) by 0 days.

(21) Appl. No.: 13/855,549

(22) Filed: Apr. 2, 2013

(65) Prior Publication Data

US 2013/0225818 A1 Aug. 29, 2013
US 2014/0163227 A2 Jun. 12, 2014

(30) Foreign Application Priority Data

Apr. 2, 2012 (IT) .............................. MI2012A0531

(51) Int. Cl.
*C07D 403/06* (2006.01)
*C07D 209/12* (2006.01)

(52) U.S. Cl.
USPC ........................................... 544/373; 548/491

(58) Field of Classification Search
None
See application file for complete search history.

(56) References Cited

FOREIGN PATENT DOCUMENTS

| | | | |
|---|---|---|---|
| CN | 102180868 | A | 9/2011 |
| CN | 102267985 | A | 12/2011 |

OTHER PUBLICATIONS

Heinrich, T. et al.; "Synthesis and Structure-Activity Relationship in a Class of Indolebutylpiperazines as Dual 5-HTIA Receptor Agonists and Serotonin Reuptake Inhibitors"; Jornal of Medicinal Chemistry, American Chemical Society; vol. 47, No. 19; Jan. 1, 2004; pp. 4584-4892.

*Primary Examiner* — Noble Jarrell
*Assistant Examiner* — John S Kenyon
(74) *Attorney, Agent, or Firm* — Gifford, Krass, Sprinkle, Anderson & Citkowski, P.C.

(57) ABSTRACT

The present invention relates, in a first aspect, to a process preparing vilazodone hydrochloride that comprises the reaction of 3-(4-chloro-1-hydroxy-butyl)-1H-indol-5-carbonitrile with 5-piperazin-1-yl-benzofuran-2-carboxylate methyl hydrochloride with the formation of a 1,4-piperazine, with subsequent dehydration, hydrogenation and treatment with ammonia, to obtain vilazodone in free base form that is then converted into the hydrochloride thereof.

15 Claims, 1 Drawing Sheet

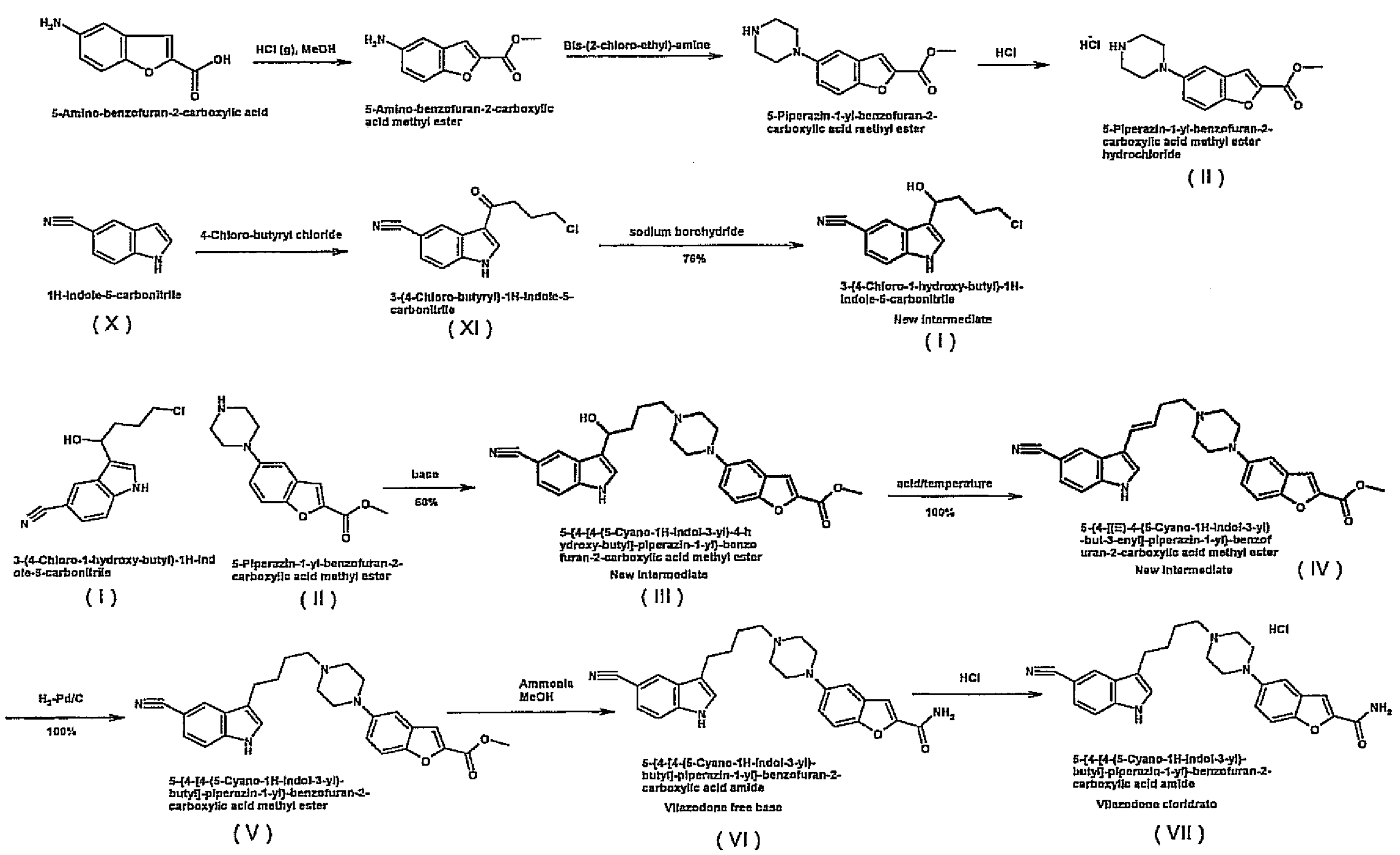

5-Amino-benzofuran-2-carboxylic acid

5-Amino-benzofuran-2-carboxylic acid methyl ester

5-Piperazin-1-yl-benzofuran-2-carboxylic acid methyl ester

5-Piperazin-1-yl-benzofuran-2-carboxylic acid methyl ester hydrochloride ( II )

1H-indole-5-carbonitrile ( X )

3-(4-Chloro-butyryl)-1H-indole-5-carbonitrile ( XI )

3-(4-Chloro-1-hydroxy-butyl)-1H-indole-5-carbonitrile

New intermediate ( I )

3-(4-Chloro-1-hydroxy-butyl)-1H-indole-5-carbonitrile ( I )

5-Piperazin-1-yl-benzofuran-2-carboxylic acid methyl ester ( II )

5-{4-[4-(5-Cyano-1H-indol-3-yl)-4-hydroxy-butyl]-piperazin-1-yl}-benzofuran-2-carboxylic acid methyl ester New intermediate ( III )

5-(4-[(E)-4-(5-Cyano-1H-indol-3-yl)-but-3-enyl]-piperazin-1-yl)-benzofuran-2-carboxylic acid methyl ester New intermediate ( IV )

5-{4-[4-(5-Cyano-1H-indol-3-yl)-butyl]-piperazin-1-yl}-benzofuran-2-carboxylic acid methyl ester ( V )

5-{4-[4-(5-Cyano-1H-indol-3-yl)-butyl]-piperazin-1-yl}-benzofuran-2-carboxylic acid amide Vilazodone free base ( VI )

5-{4-[4-(5-Cyano-1H-indol-3-yl)-butyl]-piperazin-1-yl}-benzofuran-2-carboxylic acid amide Vilazodone cloridrato ( VII )

PROCESS FOR PREPARING VILAZODONE HYDROCHLORIDE

CROSS-REFERENCE TO RELATED APPLICATIONS

This application claims priority of Italian Patent Application MI2012A000531 filed on Apr. 2, 2012.

FIELD OF THE INVENTION

The present invention relates to a process for producing vilazodone, typically in base or hydrochloride form.

The present invention originates in the sector of processes for preparing pharmacologically active substances, in particular piperazine-based substances.

BACKGROUND OF THE INVENTION

Vilazodone is the 5-5-{4-[(4-(5-Cyano-1H-indol-3-yl)butyl]-piperazin-1-yl}-benzofuran-2-carboxylate methyl molecule provided with molecular weight equal to 477.99.

From a pharmacological point of view, vilazodone is a selective serotonin reuptake inhibitor (SSRI) and a partial agonist of 5-HT1A receptors.

On account of this action thereof, vilazodone falls within the class of antidepressant drugs and finds application in the treatment of psychiatric diseases and in the treatment of major depressive syndrome (MDD) in particular.

Vilazodone and the preparation thereof were described, for example, in U.S. Pat. No. 5,532,241.

In particular two related routes of Vilazodone preparation are known.

The first synthesis route provides for the condensing of indol-5-carbonitrile with 4-chlorobutyrylchloride to give 3-(4-chlorobutyryl)-1H-indol-5-carbonitrile, which is reduced with diborane, to give 3-(4-chlorobutyl)-1H-indol-5-carbonitrile. The reaction of the latter compound with 5-(1-piperazinyl)benzofuran-2-carboxylic acid (V) leads to the expected 1,4-disubstituted piperazine 5-{4-[4-(5-cyano-1H-indol-3-yl)-4-hydroxy-butyl]-piperazin-1-yl}benzofuran-2-carboxylate methyl. Finally, the carboxyl group of the piperazine is converted into the carboxamide of interest by reaction with 2-chloro-1-methylpyridinium methanesulphonate (CMPM) and ammonia gas.

A second related synthesis route provided for hydrogenation of the 5-nitrobenzofuran-2-carboxylic acid ethyl ester with Raney nickel and H2 in MeOH to give the corresponding compound of 5-aminobenzofuran with bis(2-chloroethyl) amine in dichloromethane to give 5-(1-piperazinyl)-benzofuran-2-carboxylic acid ethyl ester. The reaction of the latter compound with di-tert-butyl dicarbonate in THF provides the protected amino compound 5-[4-(tert-butoxycarbonyl)-1-piperazinyl]benzofuran-2-carboxylic acid ethyl ester, which is first reacted with formamide and sodium alkoxide in N-methylpyrrolidone to provide the corresponding amide, and then deprotected by treatment with HCl/MeOH to give 5-(1-piperazinyl)benzofuran-2-carboxamide. Finally, this amide is condensed with 3-(4-chlorobutyl)-1H-indol-5-carbonitrile to give vilazodone.

Also known by Timo H. et al. in J. Med. Chem 2004, 47, 4684-4692 pp. 4684-4692 is a process for preparing vilazodone that provides for an initial phase in which indol-5-carbonitrile is condensed with 4-chlorobutyrylchloride to give 3-(4-chlorobutyryl)-1H-indol-5-carbonitrile, which is then reduced with sodium bis(2-methoxyethoxy)-aluminium hydride in toluene (vitride), to give 3-(4-chlorobutyl)-1H-indol-5-carbonitrile which is then reacted with 5-piperazin-1-yl-benzofuran-2-carboxylate hydrochloride to give the expected piperazine.

However, the use of a reducing agent such as vitride in the synthesis process makes it difficult to manage the production system and requires a series of precautions which make the process of the prior art hardly feasible and cost-effective from an industrial point of view. Furthermore, vitride is a particularly expensive reducing agent.

Currently, the increasing demand for vilazodone has resulted in a pressing need to avail of alternative processes for the preparation thereof.

One of the aims of the invention thus consists of providing a process for preparing vilazodone that is economically advantageous.

Another aim of the invention consists of providing a process for producing a synthesis intermediate of vilazodone without resorting to the use of vitride as reducing agent.

SUMMARY OF THE INVENTION

The Applicant, with the aim of finding alternative processes for preparing vilazodone hydrochloride in view, has surprisingly found an alternative synthesis route through novel intermediates, avoiding the use of vitride as a reducing agent.

In particular, the Applicant has found a process for preparing vilazodone hydrochloride through novel synthetic intermediates with high production yields.

In accordance with a first aspect of the invention, a process is provided for preparing vilazodone, in hydrochloride form in particular, comprising the steps of A) Reacting 3-(4-chloro-1-hydroxy-butyl)-1H-indol-5-carbonitrile of formula (I)

(I)

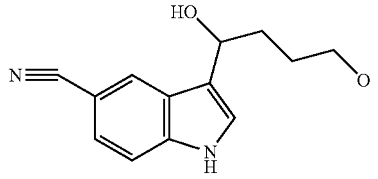

3-(4-Chloro-1-hydroxy-butyl)-1H-indole-5-carbonitrile with 5-piperazin-1-yl-benzofuran-2-carboxylate methyl hydrochloride of formula (II)

(II)

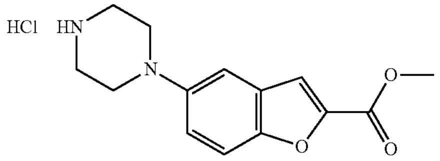

5-Piperazin-1-yl-benzofuran-2-carboxylic acid methyl ester hydrochloride to give 5-{4-[4-(5-cyano-1H-indol-3-yl)-4-hydroxybutyl]-piperazin-1-yl}benzofuran-2-carboxylate methyl of formula (III)

(III)

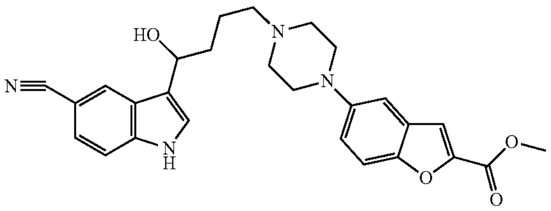

5-{4-[4-(5-Cyano-1H-indol-3-yl)-4-hydroxy-butyl]-piperazin-1-yl}-benzo furan-2-carboxylic acid methyl ester B) Treating the compound of formula (III), obtained from step A, with an acidification agent to obtain 5-{4-[4-(5-cyano-1H-indol-3-yl)-4-hydroxy-butyl]-piperazin-1-yl}benzofuran-2-carboxylate methyl of formula (IV)

(IV)

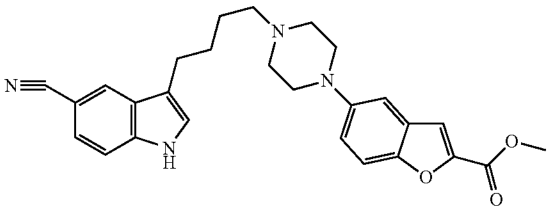

5-{4-[4-{5Cyano-1H-indol-3-yl)-butyl]-piperazin-1-yl}-benzofuran-2-carboxylic acid methyl ester C) Hydrogenating the compound obtained in step B) to obtain 5-{4-[4-(5-cyano-1H-indol-3-yl)-4-hydroxy-butyl]-piperazin-1-yl}benzofuran-2-carboxylate methyl of formula (V)

(V)

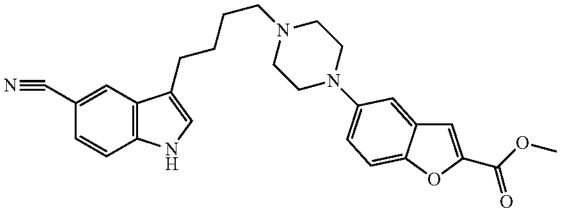

5-{4[4-(5-Cyano-1H-indol-3-yl)-butyl]-piperazin-1-yl}-benzofuran-2-carboxylic acid methyl ester D) Treating with ammonia the compound (V) obtained from step C) to obtain 5-(4-[4-(5-cyano-1H-indol-3-yl)butyl] piperazin-1-yl)benzo-furan-2-carboxamide (vilazodone in free base form)

(VI)

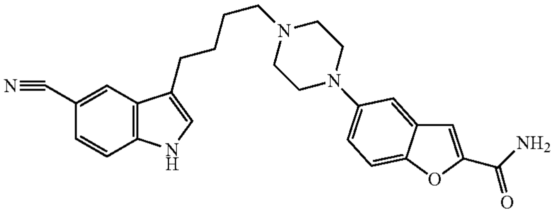

5-{4[4-(5-Cyano-1H-indol-3-yl)-butyl]-piperazin-1-yl}-benzofuran-2-carboxylic acid amide Vilazodone free base E) Treating the vilazodone in free base form obtained from step D) with hydrochloric acid to obtain vilazodone hydrochloride of formula (VII)

(VII)

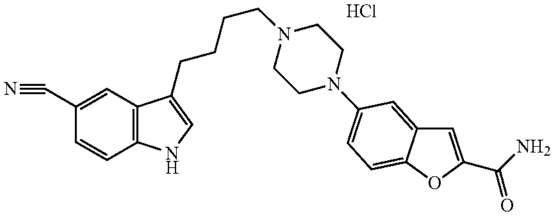

5-{4[4-(5-Cyano-1H-indol-3-yl)-butyl]-piperazin-1-yl}-benzofuran-2-carboxylic acid amide Vilazodone hydrochloride The Applicant has also surprisingly found that it is possible to obtain the starting compound 3-(4-chloro-1-hydroxy-butyl)-1H-indol-5-carbonitrile of formula (I) by operating a reduction with a selected sodium borohydride-based reducing agent.

In accordance with a second aspect, a process is thus provided for preparing a compound of formula (I) comprising reacting 5-cyanoindole (1H-indol-5-carbonitrile) of formula (X)

(X)

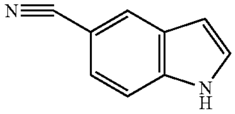

1H-indol-5-carbonitrile with 4-chlorobutyryle chloride in the presence of a suitable solvent system, to obtain 3-(4-chloro-1-hydroxy-butyl)-1H-indol-5-carbonitrile of formula (XI)

(XI)

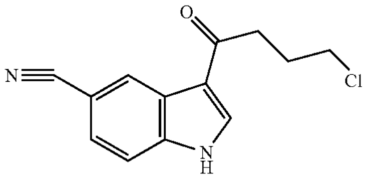

3-(4-Chloro-butyry)-1H-indole-5-carbonitrile

Reducing 3-(4-chlorobutyrryl)-1H-indol-5-carbonitrile of formula (XI) with a reducing agent to obtain 3-(4-chloro-1-hydroxy-butyl)-1H-indol-5-carbonitrile of formula (I), (I)

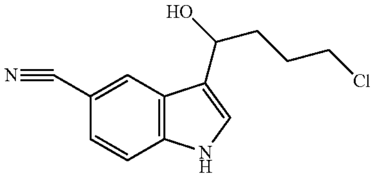

3-(4-Chloro-1-hydroxy-butyL)-1H-indole-5-carbonitrile said process being characterized in that the reducing agent used is sodium borohydride.

According to some aspects, the present invention relates to the intermediate compounds of formula (I), (III) and (IV), previously identified.

BRIEF DESCRIPTION OF THE DRAWINGS

FIG. 1 illustrates a complete diagram of the synthesis reactions of vilazodone hydrochloride of formula (VII) and of the starting compounds of formula (I) and (II).

DETAILED DESCRIPTION OF THE INVENTION

The Applicant has identified an alternative process for preparing vilazodone and the hydrochloride salt thereof, which provides for the passage through specific synthesis intermediates. The process of the invention allows vilazodone and the hydrochloride salt thereof to be produced with high purity using reducing agents that are more manageable than the ones used in conventional processes.

In accordance with a first aspect of the invention a process is provided for preparing vilazodone, in hydrochloride form in particular, comprising the steps of A) Reacting 3-(4-chloro-1-hydroxy-butyl)-1H-indol-5-carbonitrile of formula (I)

(I)

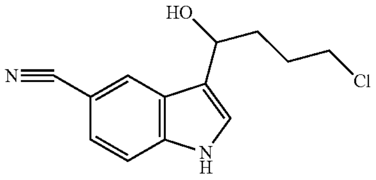

3-(4-Chloro-1-hydroxy-buty)-1H-indole-5-carbonitrile with 5-piperazin-1-yl-benzofuran-2-carboxylate methyl hydrochloride of formula (II)

(II)

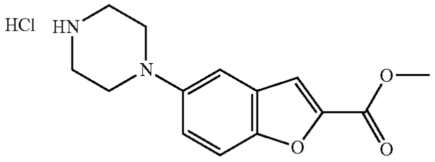

5-Piperazin-1-yl-benzofuran-2-carboxylic acid methyl ester hydrochloride in the presence of organic bases, for example amine bases, such as for example triethylamine or inorganic bases such as sodium or potassium bicarbonate, sodium or potassium carbonate, to give 5-{4-[4-(5-cyano-1H-indol-3-yl)-4-hydroxy-butyl]-piperazin-1-yl}benzofuran-2-carboxylate methyl of formula (III)

(III)

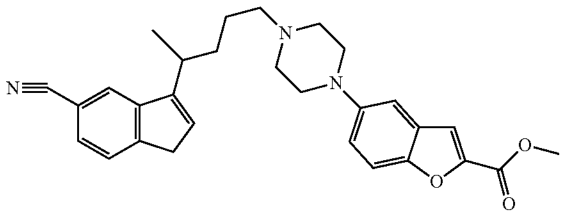

5-{4-[4-(5-Cyano-1H-indol-3-yl)-4-hydroxy-buty]-piperazin-1-yl}-benzofuran-2-carboxylic acid methyl ester B) Treating the compound obtained from step A with an acidification agent such as for example ammonium chloride to obtain 5-{4-[4-(5-cyano-1H-indol-3-yl)-4-hydroxy-butyl]-piperazin-1-yl}benzofuran-2-carboxylate methyl of formula IV (IV)

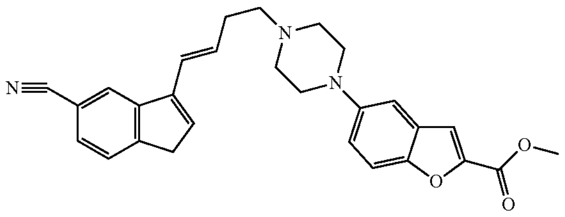

5-{4-[(E)-4-(5-Cyano-1H-indol-3-yl)-but-3-enyl]-piperazin-1-y}-benzofuran-2-carboxylic acid methyl ester C) Hydrogenating the compound of formula (IV) with $H_2$ to obtain 5-{4-[4-(5-cyano-1H-indol-3-yl)-4-hydroxy-butyl]-piperazin-1-yl}benzofuran-2-carboxylate methyl of formula (V)

(V)

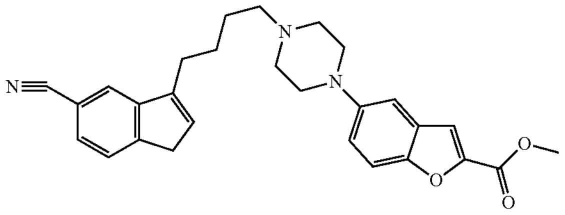

5-{4-[4-(5-Cyano-1H-indol-3-yl)-butyl]-piperazin-1-yl}-benzofuran-2-carboxylic acid methyl ester D) Treating the compound of Formula (V) obtained from step C) with ammonia to obtain 5-(4-[4-(5-cyano-1H-indol-3-yl)butyl]piperazin-1-yl)benzofuran-2-carboxamide (vilazodone in free base form) of formula (VI)

(VI)

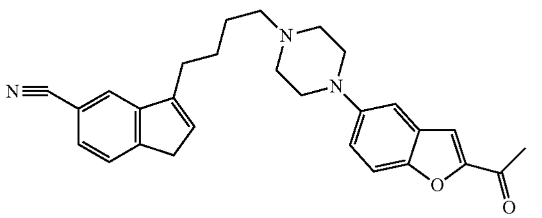

5-{4[4-(5-Cyano-1H-indol-3-yl)-butyl]-piperazin-1-yl}-benzofuran-2-carboxylic acid amide Vilazodone free base E) Optionally, treating the vilazodone in free base form obtained from step D) with hydrochloric acid to obtain vilazodone hydrochloride of formula (VII)

(VII)

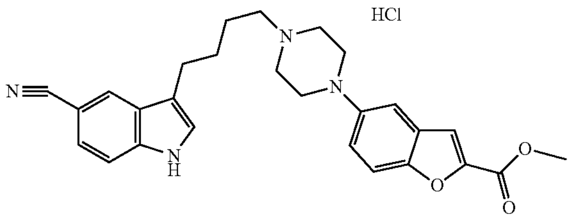

5-{4[4-(5-Cyano-1H-indol-3-yl)-butyl]-piperazin-1-yl}-benzofuran-2-carboxylic acid amide Vilazodone hydrochloride In accordance with some embodiments, step A) of the process is carried out in the presence of a suitable base.

In some embodiments, a suitable base used in step A) of the process of the invention comprises a carbonate or bicarbonate of an alkaline or alkaline-earth metal, such as for example sodium or potassium bicarbonate, sodium or potassium carbonate.

In some embodiments in step A) of the process, a dipolar aprotic solvent, such as for example N,N-dimethylacetamide, is used.

In certain embodiments, step A) of the process of the invention comprises a separation step of the organic mass using a suitable organic solvent such as, for example, ethyl acetate.

In certain embodiments the acidification agent of step B) of the process of the invention comprises a weak acid. A suitable weak acid is represented by ammonium chloride.

In certain embodiments, step B) of the method comprises heating the reaction mixture at the basis of the compound of formula (III) and the acidification agent at temperature substantially suitable for completing the reaction. A suitable temperature is comprised within the range of 80 to 110° C. By way of example temperatures in the 100° C.+/−5° C. range are particularly suitable for achieving high reaction yields in suitable timeframes.

In some embodiments, the hydrogenation step C) of the process is carried out with $H_2$ in the presence of a suitable catalyst system, such as for example Pd/C or Raney nickel.

Typically, the hydrogenation step with $H_2$ is carried out in the presence of a suitable, preferably alcoholic solvent, in particular methanol.

By way of example, step C) comprises hydrogenating the compound of formula (IV) within a hydrogenator, with a Pd/C catalyst, to 4-6%, in methanol.

In some embodiments, in step D) of the process, the compound of the formula (V) is dissolved in a suitable alcoholic solvent, typically methanol. Typically, the ammonia in gaseous form is bubbled into the solution of the compound of formula (V) in methanol until saturation of the solution.

In some embodiments, the solution treated with ammonia is distilled to obtain vilazodone base of formula (VI).

According to some embodiments, step E) of the process comprises the dissolving of vilazodone base in a suitable polar organic solvent, such as acetone for example, and treating with an HCl-based solution, at 35-39% for example, until vilazodone hydrochloride of formula (VII) is obtained.

The applicant has further identified, in accordance with other aspects of the invention, a synthesis route of the compound of formula (I) that comprises an aromatic acylation reaction followed by a reduction made with a specific sodium borohydride reducing system.

In accordance with a second aspect of the invention a process is thus provided for preparing 3-(4-chloro-1-hydroxy-butyl)-1H-indol-5-carbonitrile of formula (I) comprising i) The condensing of 1H-indol-5-carbonitrile (5-cyanoindole) of formula (X)

(X)

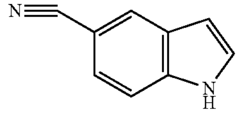

1H-indole-5-carbonitrile with 4-chlorobutyryle chloride typically in the presence of a suitable solvent system to give 3-(4-chlorobutyryl)-1H-indol-5-carbonitrile formula (XI), (XI)

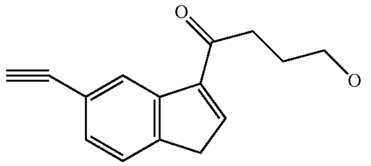

3-(4-Chloro-butyryl)-1H-indole-5-carbonitrile ii) reducing 3-(4-chlorobutyrryl)-1H-indol-5-carbonitrile of formula (XI) with a reducing agent to obtain 3-(4-chloro-1-hydroxy-butyl)-1H-indol-5-carbonitrile of formula (I), said process being characterized in that the reduction in step ii) is carried out with sodium borohydride.

According to some embodiments, step i) of the process comprises preparing a solution of 4-chlorobutyryle chloride in a chlorinated solvent, typically methylene chloride (DCM), in the presence of an activator such as aluminium chloride and the addition to this solution of another cyanoindole-based solution (1H-indol-5-carbonitrile) in a chlorinated organic solvent such as methylene chloride.

Thereafter, the resulting mixture can be poured into an aqueous solution containing HCl, typically at 30-36%. The mixture is then distilled, at a temperature falling within the range of 70 to 90° C. for example. It is then possible to extract the compound 3-(4-chlorobutyryl)-1H-indol-5-carbonitrile of formula (XI) with a suitable solvent, for example ethyl acetate.

According to some embodiments, the reducing step ii) comprises the dissolution of the sodium borohydride-based reducing agent in an alkaline aqueous solution, typically a solution of NaOH 20 to 40% by weight in water and the addition of the sodium borohydride solution to the 3-(4-chlorobutyryl)-1H-indol-5-carbonitrile of formula (XI) dissolved in a suitable organic solvent, for example tetrahydrofuran and water.

The mixture obtained is typically subjected to agitation, preferably at a temperature higher than room temperature, for example comprised between 30-40° C., for a suitable period of time, for example comprised between 2 and 4 hours, to then proceed to extraction with a suitable solvent, such as for example methylene chloride, and subsequent crystallization.

Typically, the compound 3-(4-chloro-1-hydroxy-butyl)-1H-indol-5-carbonitrile of formula (I), obtained in accordance with the second aspect of the invention, can be used as starting reagent of the process for preparing vilazodone free base or hydrochloride, in accordance with the first aspect of the present invention.

In accordance with another aspect, the present invention relates to the intermediate compound having the Formula (I)

(I)

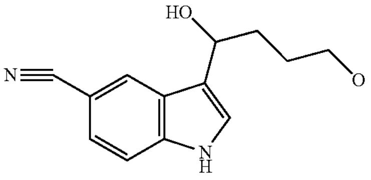

3-(4-Chloro-1-hydroxy-butyl)-1H-indole-5-carbonitrile

In accordance with another aspect, the present invention relates to the intermediate compound having the formula (III)

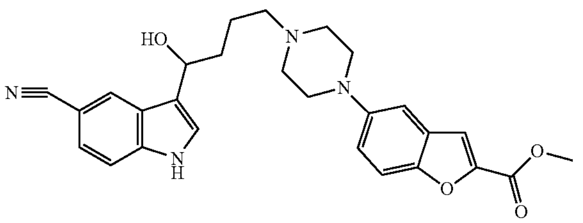

5-{4-[4-(5-Cyano-1H-indol-3-yl)-4-hydroxy-butyl]-piperazin-1-yl}-benzofuran-2-carboxylic acid methyl ester In accordance with another aspect, the present invention relates to the intermediate compound having the Formula (IV)

(IV)

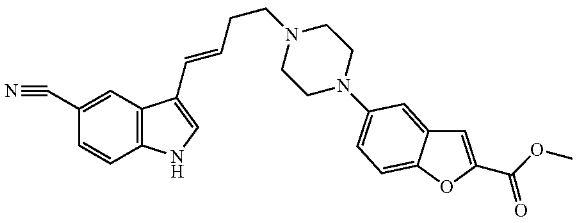

5-{4-[(E)-4-(5-Cyano-1H-indol-3-yl)-but-3-enyl]-piperazin-1-yl}-benzofuran-2-carboxylic acid methyl ester Typically, the compound 5-piperazin-1-yl-benzofuran-2-carboxylate methyl of Formula (II) can be prepared by esterifying the 5-aminobenzofuran-2-carboxylic acid with HCl, and then condensing with bis-(2-chloroethyl)amine and salifying the product obtained with HCl.

Specifically, the compound of Formula (II) 5-piperazin-1-yl-benzofuran-2-carboxylate methyl hydrochloride can be prepared by reacting 5-aminobenzofuran-2-carboxylic acid with HCl, for example by bubbling gaseous HCl, in the presence of a typically alcoholic solvent, to obtain the 5-aminobenzofuran-2-carboxylic methyl ester acid, by reacting 5-aminobenzofuran-2-carboxylic acid with bis-(2-chloroethyl)amine hydrochloride, typically in an aqueous environment and separating an organic phase containing 5-piperazin-1-yl-benzofuran-2-carboxylate methyl, by bubbling HCl in a solution containing 5-piperazin-1-yl-benzofuran-2-carboxylate methyl dissolved in a suitable dipolar aprotic solvent, such as for example N,N-dimethylformamide to obtain 5-piperazin-1-yl-benzofuran-2-carboxylate methyl hydrochloride (II).

The 5-piperazin-1-yl-benzofuran-2-carboxylate methyl of Formula (II) thus obtained by means can be used as starting material in the process for preparing vilazodone free base or hydrochloride, in accordance with the first aspect of the present invention.

FIG. 1 illustrates in detail the operating steps of one embodiment of the process of the invention and of for preparing the compounds or synthesis intermediates of Formula (I) and (II).

Specifically, in the first reaction line there is schematically illustrated the synthesis of 5-piperazin-1-yl-benzofuran-2-carboxylate methyl hydrochloride (II) by cyclization of 5-aminobenzofuran-2-carboxylic acid with bis(2-chloroethyl)amine.

In the second reaction line is schematically illustrated the synthesis of the intermediate 3-(4-chloro-1-hydroxy-butyl)-1H-indol-5-carbonitrile of Formula (I) through the condensing of indol-5-carbonitrile with 4-chlorobutyrylchloride to give 3-(4-chlorobutyryl)-1H-indol-5-carbonitrile, which is reduced with sodium borohydride, to give 3-(4-chloro-1-hydroxy-butyl)-1H-indol-5-carbonitrile.

In the third and fourth reaction line is schematically illustrated the synthesis process of vilazodone hydrochloride according to the first aspect of the invention starting from the reaction of the compounds 3-(4-chloro-1-hydroxy-butyl)-1H-indol-5-carbonitrile of Formula (I) and 5-piperazin-1-yl-benzofuran-2-carboxylate methyl hydrochloride of formula (II) through the formation of the expected 1,4-piperazine of formula (III), which by subsequent dehydration, hydrogenation and treatment with ammonia, leads to the sought after carboxamide of Formula (VI), then converted into the hydrochloride salt of Formula (VII).

The present invention will now be illustrated with reference to the following examples, which are provided for illustrative purposes only and are not to be construed as limiting of the scope of protection resulting from the claims.

Example 1

Process for Preparing 5-piperazin-1-yl-benzofuran-2-carboxylate methyl hydrochloride

Synthesis of 5-aminobenzofuran-2-carboxylic acid methyl ester

Load into a flask:

| | |
|---|---|
| 5-aminobenzofuran-2-carboxylic acid | 40 g |
| Methanol | 200 g |
| HCl gas | 10 g |

Heat the ground under reflux for 20 hours.

Dry distil and add to the residue

| | |
|---|---|
| Toluene | 40 g |
| Distilled water | 200 g |
| Ammonia 30% | 20 g |

Stir under reflux until complete dissolution

Cool at 5° C. until crystallization. Filter and wash with:

| | |
|---|---|
| Distilled water | 15 g |

Dry

There are obtained 32.3 g

Yield 74.8%

Synthesis of 5-piperazin-1-yl-benzofuran-2-carboxylate methyl hydrochloride

Load into a flask:

| | |
|---|---|
| 5-Aminobenzofuran-2-carboxylic acid methyl ester | 32 g |
| Bis-(2-chloroethyl)amine hydrochloride | 31.4 g |
| Distilled water | 128 g |

Heat under reflux, then add

| | |
|---|---|
| Sodium acetate | 43.2 g |

Stir then reflux for 1 hour then add at 30° C.

| | |
|---|---|
| Methylene chloride | 96 g |
| Ammonia | 38.4 g |

Stir at 30° C., separate the organic phase, which is dry distilled under vacuum, then add to the residue:

| | |
|---|---|
| N,N-dimethylformamide | 80 g |

Bubble in the solution

| | |
|---|---|
| HCl gas | q.s. at pH <1 |

Cool the precipitated mass at r.t., filter and wash with:

| | |
|---|---|
| Acetone | 32 g |

Dry

There are obtained 31.7 g

Yield: 63.8%

Example 2

Process for Preparing the intermediate 3-(4-Chloro-1-hydroxybutyl)-1H-indol-5-carbonitrile Synthesis of 3-(4-Chlorobutyryl)-1H-indol-5-carbonitrile Load into a flask:

| | |
|---|---|
| Aluminium trichloride | 93 g |
| Methylene chloride | 320 g |

Heat under reflux, then add:

| | |
|---|---|
| 4-chlorobutyryle chloride | 100 g |

While maintaining the reflux add a separately prepared solution of:

| | |
|---|---|
| 5-Cyano-indole | 40 g |
| Methylene chloride | 160 g |

Stir at reflux for 30 minutes then pour the reaction in a flask containing

| | |
|---|---|
| Distilled water | 400 g |
| Hydrochloric acid 32% | 32 g |

On completion of casting distil up to 80° C. Add:

| | |
|---|---|
| Ethyl acetate | 200 g |

Cool at 5° C., filter and wash with:

| | |
|---|---|
| Ethyl acetate | 60 g |
| Distilled water | 120 g |

Dry
There are obtained 58 g
Yield: 83.6%

Synthesis of the Intermediate Compound 3-(4-Chloro-1-hydroxybutyl)-1H-indol-5-carbonitrile Load into a flask:

| | |
|---|---|
| 3-(4-Chlorobutyryl)-1H-indol-5-carbonitrile | 58 g |
| Tetrahydrofuran | 116 g |
| Distilled water | 11.6 g |

Heat at 30-35° C., then add a separately prepared solution of:

| | |
|---|---|
| Distilled water | 29 g |
| 30% NaOH | 0.3 g |
| Sodium borohydride | 7 g |

Stir at 35° C. for 3 hours then add

| | |
|---|---|
| Methylene chloride | 116 g |

Stir at 35° C., separate the lower organic phase then dry then add

| | |
|---|---|
| Methanol | 72.5 g |
| Distilled water | 29 g |

Stir at 35° C. to crystallization, cool at 5° C., filter and wash with

| | |
|---|---|
| Distilled water | 11.6 g |

Dry
There are obtained 43 g
Yield: 73.5%

Example 3

Process for Preparing Vilazodone (Free Base/Hydrochloride)

Synthesis of the Intermediate 5-{4-[4-(5-Cyano-1H-indol-3-yl)-4-hydroxybutyl]-piperazin-1-yl}benzofuran-2-carboxylate methyl Load into a flask:

| | |
|---|---|
| 5-Piperazin-1-yl-benzofuran-2-carboxylate methyl hydrochloride | 11.9 g |
| Sodium bicarbonate | 6.7 g |
| N,N-dimethylacetamide | 30 g |
| Potassium iodide | 1.3 g |
| 3-(4-Chloro-1-hydroxybutyl)-1H-indol-5-carbonitrile | 12 g |

Heat at 75° C. for 28 h then add:

| | |
|---|---|
| Distilled water | 50 g |
| Ethyl acetate | 50 g |

Cool to 5° C., filter and wash with:

| | |
|---|---|
| Distilled water | 10 g |

Dry
There are obtained 11 g
Yield 58%

Synthesis of the Intermediate 5-{4-[4-(5-Cyano-1H-indol-3-yl)-but-3-enyl]-piperazin-1-yl}-benzofuran-2-carboxylate methyl Load into a flask:

| | |
|---|---|
| 5-{4-[4-(5-Cyano-1H-indol-3-yl)-4-hydroxybutyl]-piperazin-1-yl}-benzofuran-2-carboxylate methyl | 3 g |
| DMA | 15 g |
| Ammonium chloride | 0.32 g |

Heat the mixture at 100° C. for 7 hours

Cool to 20° C. then add

| | |
|---|---|
| Ethyl acetate | 25 g |
| Aqueous solution of sodium bicarbonate 10% | 10 g |

Stir and separate the organic phase, then distil to an oily residue

Dissolve all the residue (4.3 g) obtained in

| | |
|---|---|
| Methanol | 25 g |

and transfer the solution thus obtained directly into the hydrogenator for the next step

Synthesis of 5-{4-[(4-(5-Cyano-1H-indol-3-yl)-butyl]-piperazin-1-yl}-benzofuran-2-carboxylate methyl Load into the hydrogenator the solution of 5-{4-[4-(5-Cyano-1H-indol-3-yl)-but-3-enyl]-piperazin-1-yl}-benzofuran-2-carboxylate methyl

| | |
|---|---|
| 5-{4-[4-(5-Cyano-1H-indol-3-yl)-but-3-enyl]-piperazin-1-yl}-benzofuran-2-carboxylate methyl crude oil | 4.3 g |
| in Methanol | 25 g |
| Pd/C 5% | 0.4 g |

Hydrogenate at 15-30° C. at 1.5 bar for 2 hours

Filter the catalyst on cardboard and distil the filtrate to wet crude oily residue.

Dissolve this residue (approx. 4 g) in

| | |
|---|---|
| Methanol | 10 g |

and use this solution directly for the next step

Synthesis of Vilazodone Base

In the solution of

| | |
|---|---|
| 5-{4-[(4-(5-Cyano-1H-indol-3-yl)butyl]-piperazin-1-yl}-benzofuran-2-carboxylate methyl crude oil | 4 g (approx.) |
| in Methanol | 100 g |

Bubble ammonia gas until saturation of the solution.

Stir at room temperature for 20 hours

Then distil the solution to a solid residue of Vilazodone base (approx. 3 g) that is used directly for the next step.

Synthesis of Vilazodone Hydrochloride

| | |
|---|---|
| Vilazodone base | 2 g |
| Acetone | 12 g |

Stir under reflux until complete dissolution of the powder, then load:

| | |
|---|---|
| HCl 37% | 0.45 g |

Cool to 45° C. (a precipitate is formed).

Cool to 5° C. then filtered and wash with acetone (5 g).

Dry 55° C.

There are obtained approximately 1.5 g of Vilazodone hydrochloride.

The invention claimed is:

1. A process for preparing vilazodone, or a hydrochloride form thereof comprising the steps of A) reacting 3-(4-chloro-1-hydroxy-butyl)-1H-indol-5-carbonitrile of formula (I)

(I)

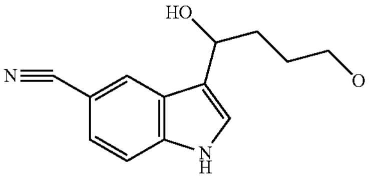

3-(4-Chloro-1-hydroxy-butyl)-1H-indole-5-carbonitrile with 5-piperazin-1-yl-benzofuran-2-carboxylate methyl hydrochloride of formula (II)

(II)

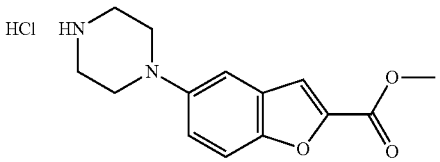

5-Piperazin-1-yl-benzofuran-2-carboxylic acid methyl ester hydrochloride to give 5-{4-[4-(5-cyano-1H-indol-3-yl)-4-hydroxybutyl]-piperazin-1-yl}benzofuran-2-carboxylate methyl of formula (III)

(III)

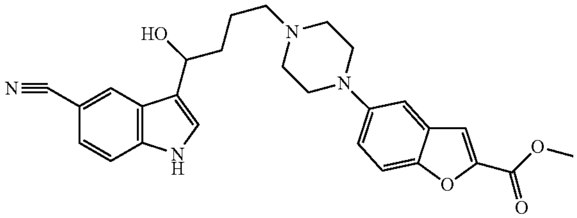

5-{4-[4-(5-Cyano-1H-indol-3-yl)-4-hydroxy-butyl]-piperazin-1-yl}-benzofuran-2-carboxylic acid methyl ester B) treating the compound of formula (III), obtained from step A, with an acidification agent to obtain 5-{4-[4-(5- cyano-1H-indol-3-yl)-4-hydroxy-butyl]-piperazin-1-yl}benzofuran-2-carboxylate methyl of formula (IV)

(IV)

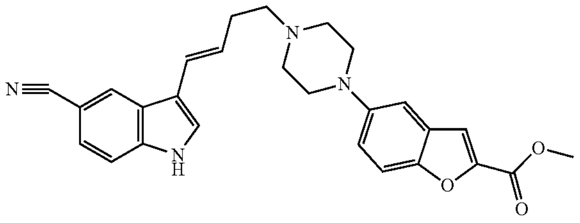

5-{4-[(E)-4-(5-Cyano-1H-indol-3-yl)-but-3-enyl]-piperazin-1-yl}-benzofuran-2-carboxylic acid methyl ester C) hydrogenating the compound of formula (IV) with $H_2$ to obtain 5-{4-[4-(5-cyano-1H-indol-3-yl)-4-hydroxy-butyl]-piperazin-1-yl}benzo-furan-2-carboxylate methyl of formula (V)

(V)

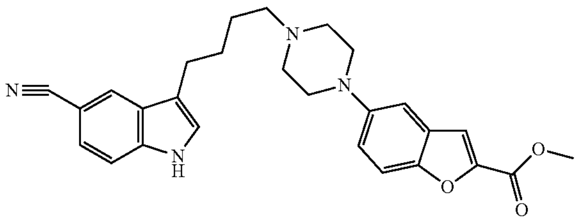

5-{4-[4-(5-Cyano-1H-indol-3-yl)-butyl]-piperazin-1-yl}-benzofuran-2-carboxylic acid methyl ester D) treating the compound of formula (V) obtained from step C) with ammonia to obtain 5-(4-[4-(5-cyano-1H-indol-3-yl)butyl]piperazin-1-yl)benzo-furan-2-carboxamide of formula (VI), (VI)

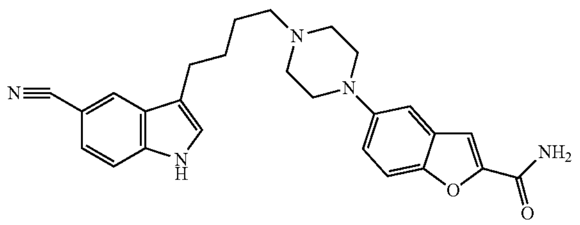

5-{4-[4-(5-Cyano-1H-indol-3-yl)-butyl]-piperazin-1-yl}-benzofuran-2-carboxylic acid amide
Vilazodone free base E) optionally treating the compound of formula (VI) with hydrochloride acid to obtain vilazodone hydrochloride of formula (VII)

(VII)

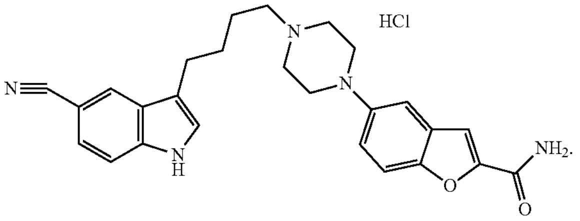

5-{4-[4-(5-Cyano-1H-indol-3-yl)-butyl]-piperazin-1-yl}-benzofuran-2-carboxylic acid amide
Vilazodone hydrochloride

2. The process according to claim 1, wherein step A) is carried out in the presence of a weak base and an organic solvent.

3. The process according to claim 2, wherein the weak base is sodium bicarbonate and the organic solvent is a dipolar aprotic solvent.

4. The process according to claim 2 wherein the organic solvent is N,N-dimethylacetamide.

5. The process according to claim 1 wherein the acidification agent in step B) is ammonium chloride.

6. The process according to claim 1, wherein step B) comprises heating the compound of formula (III) in a mixture with N,N-dimethylacetamide and ammonium chloride.

7. The process according to claim 1 wherein the hydrogenation step C) with $H_2$ is carried out in the presence of a Pd/C or Raney nickel catalyst and an alcoholic solvent.

8. The process according to claim 1 wherein in step D) the compound of formula (V) is dissolved in an alcoholic solvent, wherein gaseous ammonia is bubbled.

9. The process according to claim 8 wherein the alcoholic solvent is methanol.

10. The process according to claim 1, further comprising preparing the compound of formula (I), through the steps of i) condensing 1H-indol-5-carbonitrile (5-cyanoindole) of formula (X)

(X)

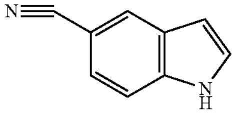

1H-Indole-5-carbonitrile with 4-chlorobutyryl chloride to give 3-(4-chlorobutyryl)-1H-indol-5-carbonitrile of formula (XI), (XI)

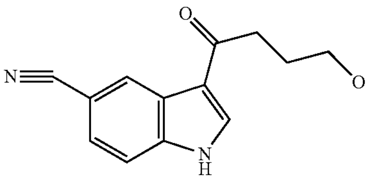

3-(4-Chloro-butyryl)-1H-indole-5-carbonitrile ii) reducing 3-(4-chlorobutyrryl)-1H-indol-5-carbonitrile of formula (XI) with a reducing agent to obtain 3-(4-chloro-1-hydroxy-butyl)-1H-indol-5-carbonitrile of formula (I), wherein the reduction reaction in step ii) is carried out with sodium borohydride.

11. The process according to claim 10, wherein step i) comprises preparing a solution of 4-chlorobutyrryl in a chlorinated organic solvent, selected from methylene chloride, in the presence of an activating agent, selected from aluminum chloride, and adding the solution containing 1H-indol-5-carbonitrile in a chlorinated organic solvent, selected from methylene chloride, to this solution.

12. The process according to claim 10 wherein step ii) comprises dissolving the sodium borohydride reducing agent in an alkaline aqueous solution and adding the sodium borohydride solution to 3-(4-chlorobutyrryl)-1H-indol-5-carbonitrile of formula (XI) dissolved in a suitable organic solvent, selected from tetrahydrofuran and water.

13. A compound which is an intermediate of the process of claim 1 having the formula (I)

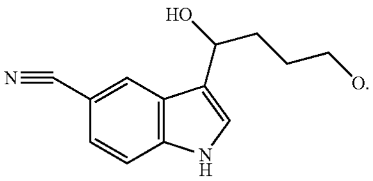

3-(4-Chloro-1-hydroxy-butyl)-1H-indole-5-carbonitrile

14. A compound which is an intermediate of the process of claim 1 having the formula (III)

(III)

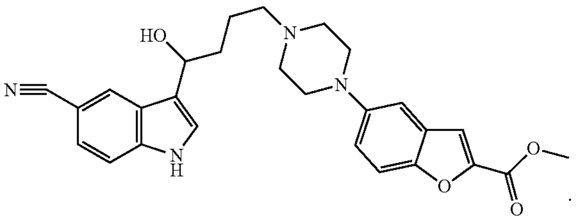

5-{4-[4-(5-Cyano-1H-indol-3-yl)-4-hydroxy-butyl]-piperazin-1-yl}-benzofuran-2-carboxylic acid methyl ester

15. A compound which is an intermediate of the process of claim 1 having the formula (IV)

(IV)

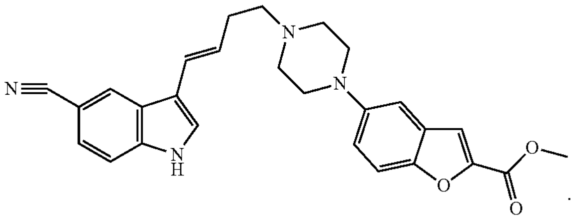

5-{4-[(E)-4-(5-Cyano-1H-indol-3-yl)-but-3-enyl]-piperazin-1-yl}-benzofuran-2-carboxylic acid methyl ester

* * * * *

UNITED STATES PATENT AND TRADEMARK OFFICE

CERTIFICATE OF CORRECTION

PATENT NO. : 8,802,851 B2
APPLICATION NO. : 13/855549
DATED : August 12, 2014
INVENTOR(S) : Massimo Ferrari et al.

It is certified that error appears in the above-identified patent and that said Letters Patent is hereby corrected as shown below:

In the Claims:

At column 18, claim number 10, line number 60, Delete (XI)

"

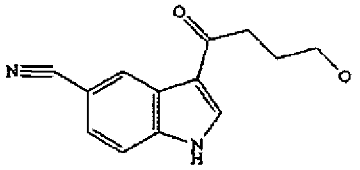

3-(4-Chloro-butyryl)-1H-indole-5-carbonitrile

", Insert --

(XI)

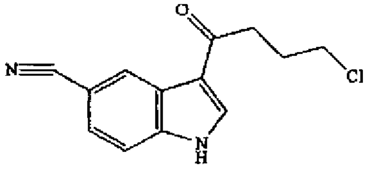

3-(4-Chloro-butyryl)-1H-indole-5-carbonitrile

--

At column 19, claim number 13, line number 27, Delete

"

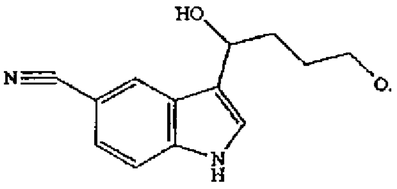

3-(4-Chloro-1-hydroxy-butyl)-1H-indole-5-carbonitrile

", Insert --

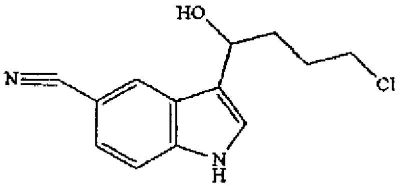

3-(4-Chloro-1-hydroxy-butyl)-1H-indole-5-carbonitrile

--

Signed and Sealed this
Twenty-ninth Day of September, 2015

Michelle K. Lee
*Director of the United States Patent and Trademark Office*